(12) United States Patent
Kim

(10) Patent No.: US 7,422,722 B2
(45) Date of Patent: Sep. 9, 2008

(54) NIPPLE STERILIZER

(76) Inventor: Yong Tae Kim, Shain Village 205-301, 33/3 121-11, Wonjong-Dong Ojeong-Gu, Bucheon, Gyeonggi-Do 421-200 (KR)

( * ) Notice: Subject to any disclaimer, the term of this patent is extended or adjusted under 35 U.S.C. 154(b) by 343 days.

(21) Appl. No.: 10/595,207

(22) PCT Filed: Sep. 24, 2004

(86) PCT No.: PCT/KR2004/002457

§ 371 (c)(1),
(2), (4) Date: Mar. 23, 2006

(87) PCT Pub. No.: WO2005/030274

PCT Pub. Date: Apr. 7, 2005

(65) Prior Publication Data

US 2008/0124257 A1     May 29, 2008

(30) Foreign Application Priority Data

Sep. 30, 2003     (KR) ...................... 10-2003-0067860

(51) Int. Cl.
*A01L 2/00* (2006.01)
*A01L 2/10* (2006.01)
(52) U.S. Cl. .................. 422/24; 422/300; 422/302; 422/186.3

(58) Field of Classification Search .................. 422/24, 422/300, 302, 186.3
See application file for complete search history.

(56) References Cited

U.S. PATENT DOCUMENTS

| 2,088,658 | A | * | 8/1937 | Meyerson | .................... 422/303 |
| 2,316,145 | A | * | 4/1943 | Futrell | ........................ 422/300 |
| 2,546,681 | A | * | 3/1951 | Searer | ........................ 215/11.5 |
| 5,166,528 | A | * | 11/1992 | Le Vay | .................. 250/455.11 |
| 2006/0165571 | A1 | * | 7/2006 | Seon | .......................... 422/302 |

FOREIGN PATENT DOCUMENTS

| JP | 00015040 | 1/1998 |
| JP | 2001-178799 | 7/2001 |
| JP | 00191678 | 7/2002 |
| KR | 1020000018110 | 4/2000 |

* cited by examiner

*Primary Examiner*—Nikita Wells
(74) *Attorney, Agent, or Firm*—IPLA P.A.; James E. Bame

(57) ABSTRACT

The invention relates to a nipple sterilizer which may easily sterilize the nipple of a nursing bottle. According to an aspect of the invention, there is provided a nipple sterilizer comprising a body 10 which has an opening 12 at its lower surface and is to be mounted at a nursing bottle 2 in order that the nipple 6 of the bottle 2 may be inserted through the opening 12 and may be covered thereby, a sterilization lamp 20 which is positioned inside the body 10 and sterilizes the nipple 6, an electric power source 30 which is positioned inside the body 10 in order to be connected to the sterilization lamp 20, a switch 40 which is electrically connected between the electric power source 30 and the sterilization lamp 20 and makes the sterilization lamp 20 switched on and off.

3 Claims, 5 Drawing Sheets

[Fig. 1]
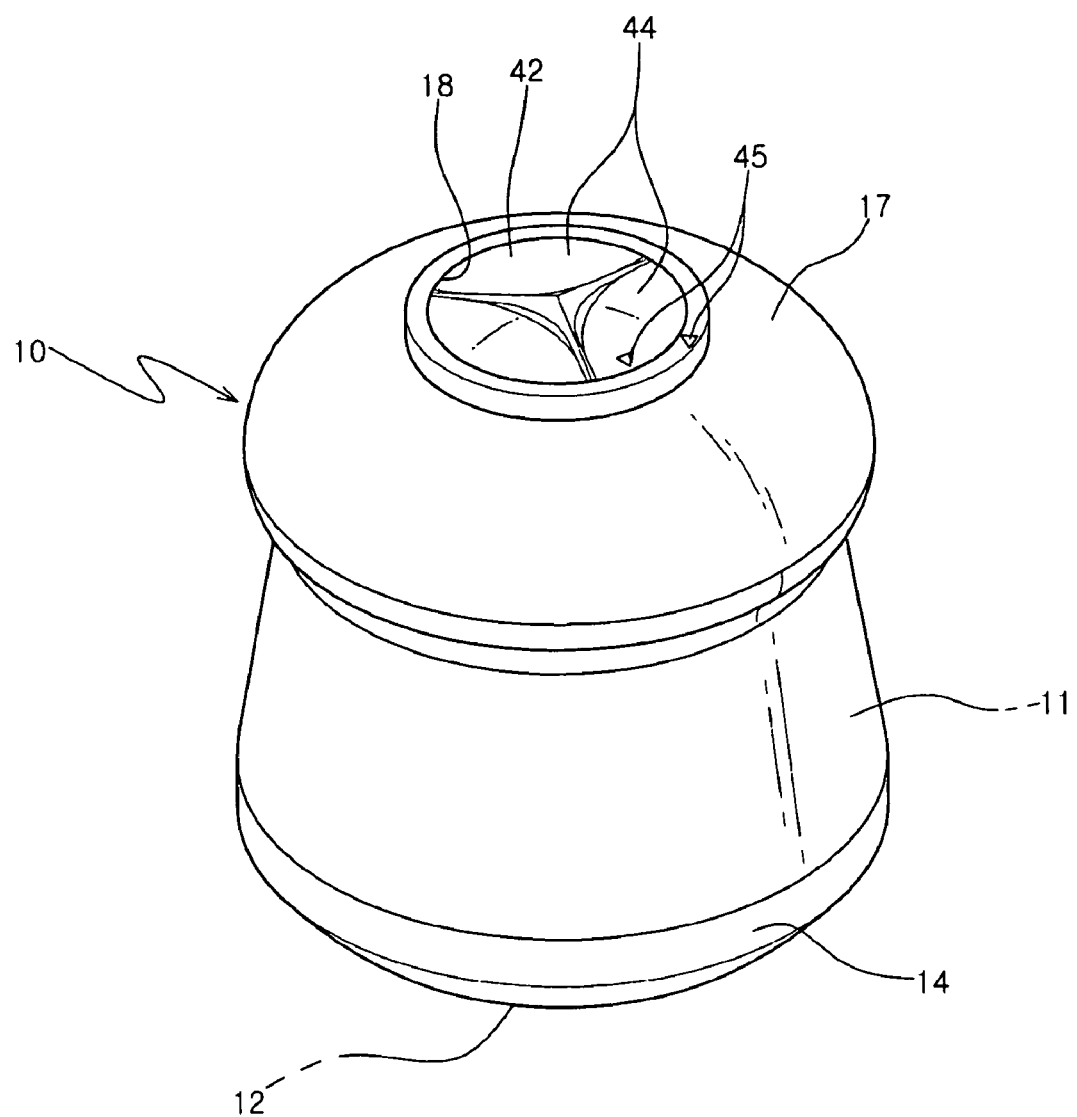

[Fig. 2]
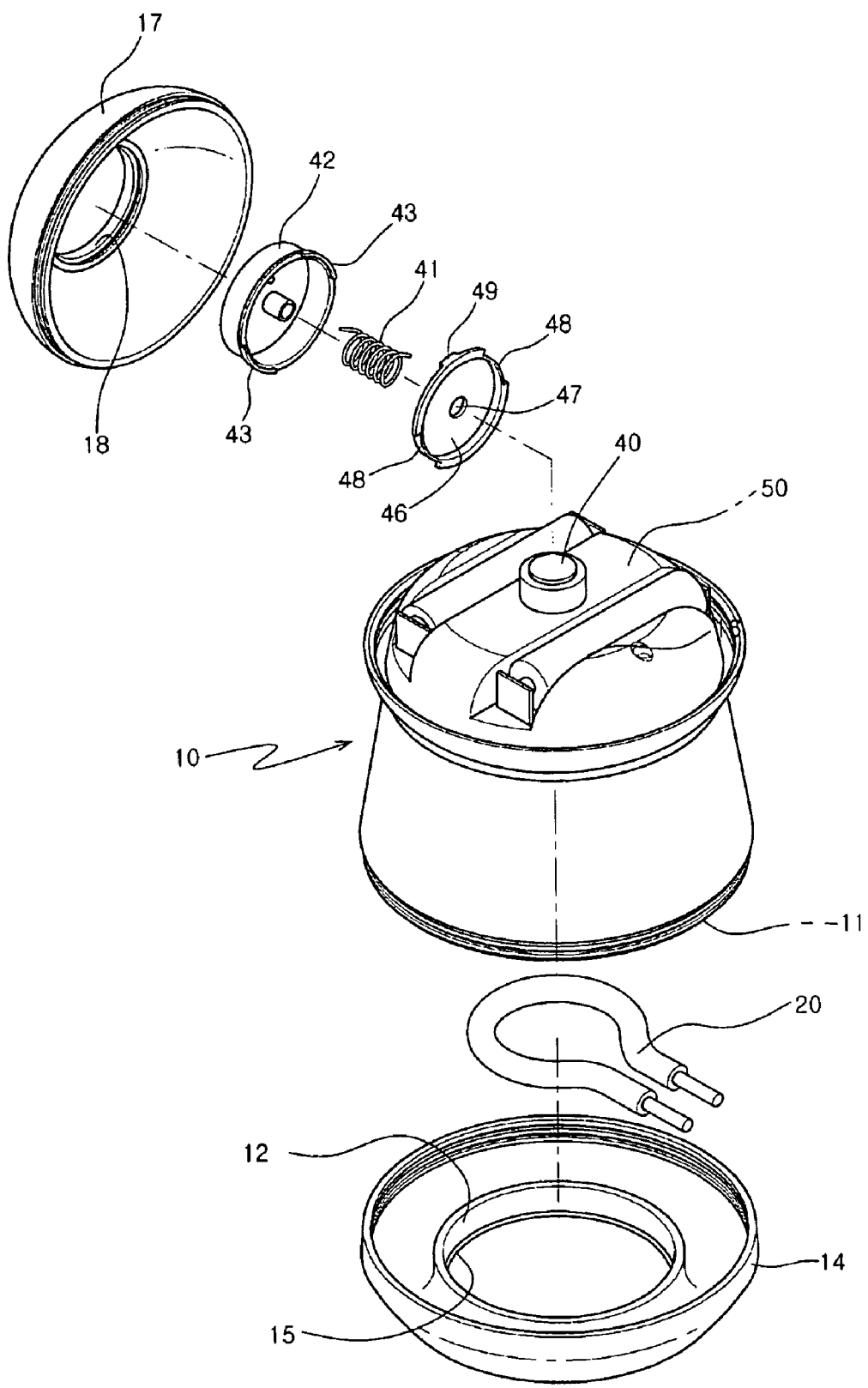

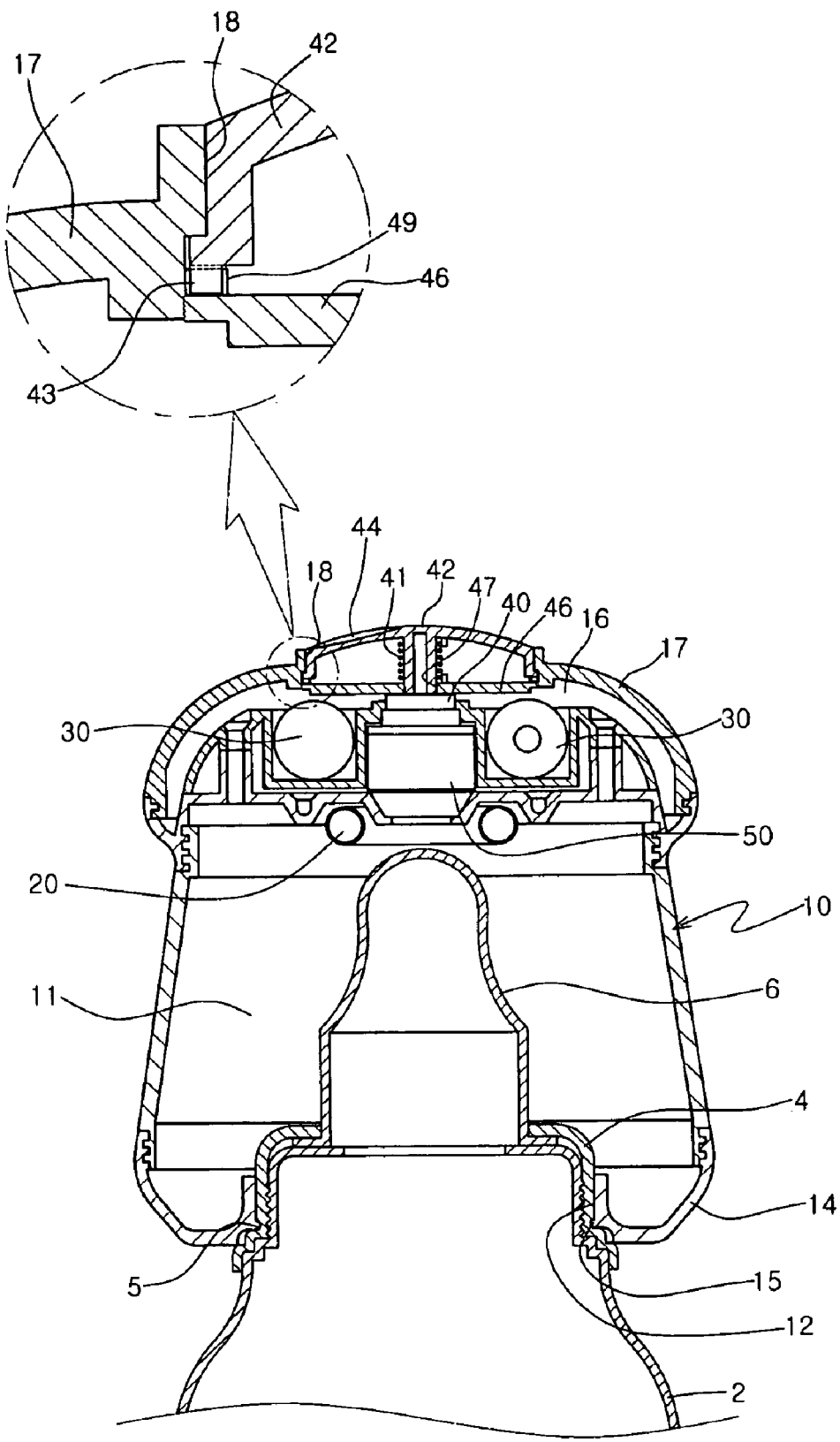
[Fig. 3]

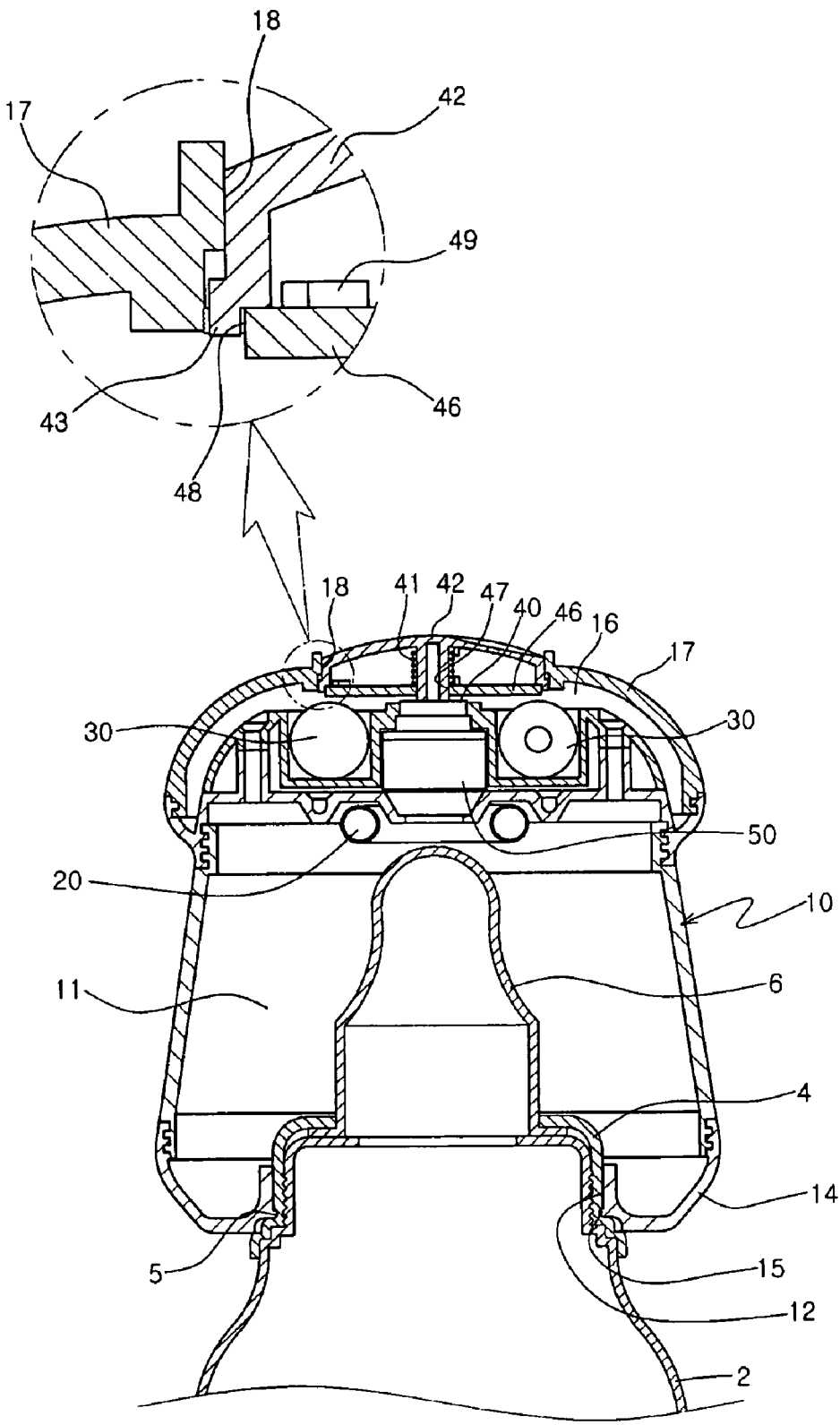
[Fig. 4]

[Fig. 5]
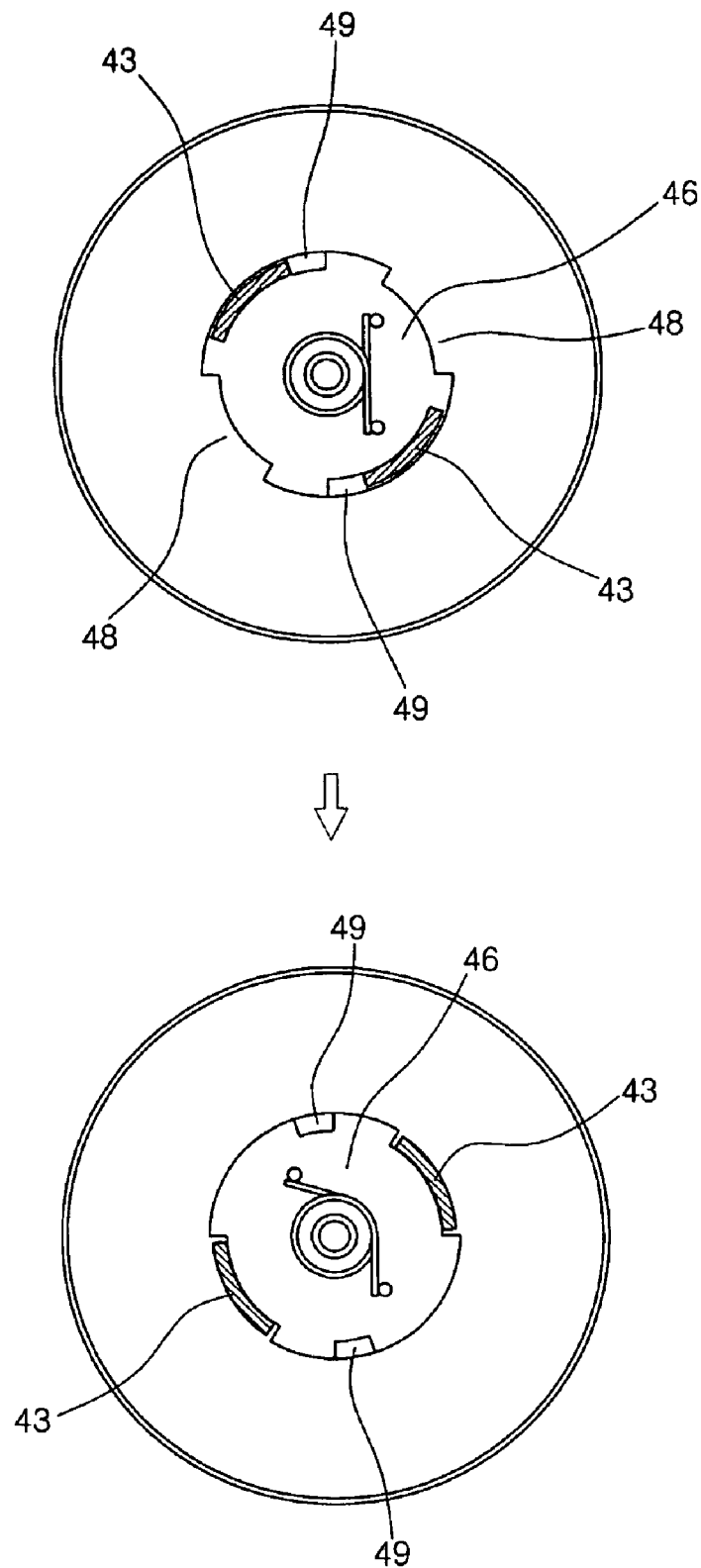

NIPPLE STERILIZER

FIELD OF THE INVENTION

The invention relates to a nipple sterilizer, and more particularly, relates to a nipple sterilizer which may easily sterilize the nipple of a nursing bottle.

BACKGROUND OF THE INVENTION

Generally, in case of the mothers who cannot feed their babies with breast milk, they feed their babies with milk, powder milk or weaning diet by use of a nursing bottle composed of a plastic container and a silicon rubber nipple at the top end of the container.

Here, after using the nursing bottle, the user generally sterilizes the bottle in boiling water or in a sterilizing device and the like in order that they may sanitarily use the bottle later.

However, it is so troublesome for the user to sterilize the nursing bottle in hot water or in a sterilizing device whenever they use it. Particularly, when they go out of doors or travel, it is difficult to boa the water or to carry along the sterilization device. Accordingly, there is a problem that the users cannot sterilize the nursing bottle while they go out of doors or travel.

DETAILED DESCRIPTION OF THE INVENTION

The invention is created to solve the above described problems and so the object of the invention is to provide a nipple sterilizer wherein the user may conveniently sterilize the nipple when they stay at home as well as when they go out of doors or travel, and which the users may easily carry along with them.

According to an aspect of the invention, there is provided a nipple sterilizer comprising:

a body 10 which has an opening 12 at its lower surface and is to be mounted at a nursing bottle 2 in order that the nipple 6 of the bottle 2 may be inserted through the opening 12 and may be covered thereby;

a sterilization lamp 20 which is positioned inside the body 10 and sterilizes the nipple 6;

an electric power source 30 which is positioned inside the body 10 in order to be connected to the sterilization lamp 20;

a switch 40 which is electrically connected between the electric power source 30 and the sterilization lamp 20 and makes the sterilization lamp 20 switched on and off;

wherein the body 10 is mounted at the nursing bottle 2 and serves as a cap for covering the ripple 6, and wherein a user may easily sterilize the ripple 6 only if he/she touches the switch 40 at the state that the nipple 6 is covered by the body 10.

According to another aspect of the invention, there is provided a nipple sterilizer:

wherein the nipple 6 is inserted into an adaptor 4 which is screwed at the nursing bottle 2, and the body 10 may be detachably engaged with the nursing bottle 2 by one or more grooves 5 and jaws 15 which are respectively formed at the periphery of the adaptor 4 and the inner wall of the opening 19 of the body 10.

According to another aspect of the invention, there is provided a nipple sterilizer:

wherein a nob 42 is protruded out of the upper surface of the body 10 and is elastically supported by a spring 41 which is positioned inside the body 10, one or more projections 43 are protruded out of one end of the nob 42, a support member 46 is mounted at the upper portion of the body 10 and the projections 43 of the nob 42 are blocked by the support member 46 in order that the nob 42 may not be pressed, and one or more grooves 48 are formed at the periphery of the support member 46 in order that the blocking of the projections 43 may be released, and wherein the nob 42 may be pressed as the projections 43 of the nob 42 be aligned with the grooves 48 of the support member 46 if a user rotates the nob 42 toward one direction so that the switch 40 may be pressingly switched on by the nob 42.

BRIEF DESCRIPTION OF THE DRAWINGS

FIG. 1 is a perspective view of a nipple sterilizer of the invention.

FIG. 2 the dissembled view of FIG. 1

FIG. 3 and FIG. 4 are respectively side views showing the operation of the nipple sterilizer.

FIG. 5 is a top view showing the operation of the nipple sterilizer.

THE PREFERRED EMBODIMENT OF THE INVENTION

A preferred embodiment of the invention will be described in detail below by referring to the accompanying drawings. FIG. 1 to FIG. 5 show one embodiment of a nipple sterilizer according to the invention. Referring to the drawings, the nipple sterilizer includes a body 10 which is to be engaged at a nursing bottle 2 having a nipple 6 as a cap type and a sterilization lamp 20 in the body 10 so that a user may easily sterilize the nipple 6 by the sterilization lamp 20 after combining the body 10 at the nursing bottle 2.

Here, the nipple 6 is to be engaged at the opening of the nursing bottle 2 by a circular adaptor 4, and grooves 5 are formed at the outer periphery of the adaptor 4. Accordingly, the body 10 may be detachably engaged at the grooves 5.

The inner space of the body 10 is divided into a sterilization chamber 11 at the upper portion and a driving chamber 16 at the lower portion. Here, the sterilization chamber 11 is preferably formed with able synthetic resin in order that the user may easily watch the sterilization lamp 20 positioned in the inner space of the sterilization chamber 11. And, an opening 12 is formed at the lower surface of the sterilization chamber 11 in order that the ripple 6 of the nursing bottle 2 may be inserted through the opening 12 and jaws 15 to be engaged with the groove 5 are formed at the inner wall of the opening 12 so that the body 10 may be detachably engaged with the adaptor 4 of the nursing bottle 2 by the jaws 15.

Here, the opening 12 is formed at a ring member 14 screwed at the sterilization chamber 11. Therefore, the user may replace the sterilizer of the invention by exchanging the adaptor 4 in accordance with the standard of the nursing bottle 2.

And, a sterilization lamp 20 is positioned at the upper portion of the sterilization chamber 11. The sterilization lamp 20 radiates ultraviolet rays and ozone to sterilize microorganism such as bacteria, germ or virus which exists at the ripple 6. Here, the sterilization lamp 20 is formed in ring shape in order that it may be engaged at the periphery of the ripple 6 and may uniformly sterilize the ripple 6.

Further, a switch 40 is mounted at the central portion of the bottom of the driving chamber 16 and the sterilization lamp 20 may be switched on and off by the switch 40. And, a plurality of batteries 30 are positioned at the periphery of the switch 40 and electric power may be supplied to the sterilization lamp 20 by the batteries 30. Accordingly, the batteries 30 are used as the electric power source for the sterilization lamp 20 so that the user may use the invention even at the outdoor place where the electric power cannot be supplied. And, the switch 40 and the sterilization lamp 20 are connected to a control portion 50, and a timer (not shown) is mounted in the control portion 50 so that electric power may be applied to the sterilization lamp 20 by the timer for a preset time, so to speak, about eight minutes and the ripple 6 may be sterilized by the sterilization lamp 20.

And, a cover 17 is screwed at the upper portion of the driving chamber 16 so that the user may detach the cover 17 and exchange the batteries 30 in the driving chamber 16. Here, a hole 18 penetrating toward the driving chamber 16 is formed at the central portion of the cover 17, and a nob 42 elastically supported by a spring 41 is protruded out of the upper portion of the body 10 through the hole 18. The nob 42 is to switch on the switch 40 in the driving chamber 16, and it is engaged at the hole 18 rotatably as well as slidably toward lower and upper direction. Here, a plurality of projections 43 of arc shape are protruded at the periphery of the lower surface of the nob 42 along the peripheral direction in equal gap, a grip groove 44 is formed at the upper surface of the nob 42 in order to rotate the nob 42 easily.

Here, a support member 46 is positioned at the lower surface of the nob 42 and the upper surface of the support member 46 is to be engaged with the projection of the nob. The support member 46 is engaged with the projection 43 of the nob 42 and supports the nob 42 in order that the nob 42 may not be pressed accidentally. And, grooves 48 are formed at the periphery of the support member 42 so that, when the user rotates the nob 42 toward one direction, the projections 43 of the nob 42 may be released and the nob 42 may be pressed. Accordingly, if the user rotates the nob 42 toward one direction and makes the projections 43 of the nob 42 meet with the grooves 48 of the support member 46, the nob 42 may be pressed. And, a stopper 49 is formed at one portion of the grooves 48 and is protruded toward the upper direction and when the nob 42 is returned to the original state by a spring 41, the projections 43 of the nob 42 are engaged with the stopper 49 so that the nob 42 is not rotated. And, a penetration hole 47 is formed at the central portion of the support member 46 so that the lower end of the nob 42 may press the switch 40 through the penetration hole 47 and the switch 40 may be switched on.

Here, the spring 41 is formed with a tortion spring which may elastically support the nob 42 toward the upper direction and may elastically support the projections 43 of the nob 43 toward the stopper 49 of the support member 46. Accordingly, as shown in FIG. 3 to FIG. 5, the projections 43 of the nob 42 is elastically supported toward the stopper 49 of the support member 46 by the spring 41 so that the projections 43 are engaged with the upper surface of the support member 46 and the nob 42 is not pressed. Next, if the user rotates the nob 42 toward one direction in order that the projections 43 of the nob 42 and the insertion 48 of the support member 46 may meet each other. In this state, if the user may press the nob 42 toward the switch 40, the projections 43 of the nob 42 is inserted into the insertion groove 48 of the support member 46 and the nob 42 is pressed so that the switch 40 is switched on and electric power may be applied to the sterilization lamp 20.

Accordingly, because the sterilization lamp 20 is not lighted although the nob 42 is pressed accidentally or an infant presses the nob 42, the user may use the invention safely.

Non-described numeral 45 are position display portions which has been displayed at one side of the upper surface of the nob 42 and that of the upper surface of the penetration hole 18 for displaying the positions of the projections 43 and the grooves 48. Accordingly, if the user matches these position display portions 45, the nob 42 may be pressed.

According to the nipple sterilizer of the invention, as shown in FIG. 3 and FIG. 4, the user may reserve the nipple sterilizer of the invention in a cap type of a nursing bottle 2 by combining the body 10 at the adaptor 4 in order to cover the nipple 6 of the nursing bottle 2. And, if the user rotates the nob 42 positioned at the upper side of the body 10 toward one direction and pressed it, the switch 40 may be switched on by the nob 42 so that electric power of the batteries 30 may be applied to the sterilization lamp 20 and the nipple 6 may be sterilized for about eight minutes by the sterilization lamp 20.

INDUSTRIAL APPLICABILITY

According to the above described invention, the nipple sterilizer has an advantage that the body may be engaged with the nipple in a cap type so that alien material is not stuck to the nipple. And, the invention has the advantage that, if the user rotate the nob toward one direction to press the nob, the nipple may be sterilized by the sterilization lamp so that the user may use the invention much more conveniently than sterilizing the nipple in boiling water or in a sterilization device. And, the invention has the advantage that batteries are used for electric power so that the user may combine the body at the nursing bottle as a cap and may carry along the invention even when they go out of doors or travel. Further, the nipple sterilizer has the advantage the user may switch on the switch only when they rotate the nob and press it so that the sterilization lamp is not operated although the nob is pressed accidentally or the infant presses the nob curiously and the user may use the invention safely.

The invention claimed is:

1. A nipple sterilizer comprising:
   a body 10 which has an opening 12 at its lower surface and is to be mounted at a nursing bottle 2 in order that the nipple 6 of the bottle 2 may be inserted through the opening 12 and may be covered thereby;
   a sterilization lamp 20 which is positioned inside the body 10 and sterilizes the nipple 6;
   an electric power source 30 which is positioned inside the body 10 in order to be connected to the sterilization lamp 20;
   a switch 40 which is electrically connected between the electric power source 30 and the sterilization lamp 20 and makes the sterilization lamp 20 switched on and off;
   wherein the body 10 is mounted at the nursing bottle 2 and serves as a cap for covering the nipple 6, and wherein a user may easily sterilize the nipple 6 only if he/she touches the switch 40 at the state that the nipple 6 is covered by the body 10.

2. A nipple sterilizer of claim 1, wherein the nipple 6 is inserted into an adaptor 4 which is screwed at the nursing bottle 2, and the body 10 may be detachably engaged with the nursing bottle 2 by one or more grooves 5 and jaws 15 which are respectively formed at the periphery of the adaptor 4 and the inner wall of the opening 19 of the body 10.

3. A nipple sterilizer, wherein a nob 42 is protruded out of the upper surface of the body 10 and is elastically supported by a spring 41 which is positioned inside the body 10, one or more projections 43 are protruded out of one end of the nob 42, a support member 46 is mounted at the upper portion of the body 10 and the projections 43 of the nob 42 are blocked by the support member 46 in order that the nob 42 may not be pressed, and one or more grooves 48 are formed at the periphery of the support member 46 in order that the blocking of the projections 43 may be released, and wherein the nob 42 may be pressed as the projections 43 of the nob 42 be aligned with the grooves 48 of the support member 46 if a user rotates the nob 42 toward one direction so that the switch 40 may be pressingly switched on by the nob 42.

* * * * *